United States Patent
Wang et al.

(10) Patent No.: US 7,498,327 B2
(45) Date of Patent: Mar. 3, 2009

(54) INDOLYLALKYLAMINE METABOLITES AS 5-HYDROXYTRYPTAMINE-6 LIGANDS

(75) Inventors: Youchu Wang, St. Laurent (CA); Chia-Cheng Shaw, St. Laurent (CA); Ronald Charles Bernotas, Royersford, PA (US); Chung-Chiee Paul Wang, Plainsboro, NJ (US); Ping Cai, New City, NY (US); Zhi Wang, Malvern, PA (US)

(73) Assignee: Wyeth, Madison, NJ (US)

( * ) Notice: Subject to any disclaimer, the term of this patent is extended or adjusted under 35 U.S.C. 154(b) by 521 days.

(21) Appl. No.: 11/158,702

(22) Filed: Jun. 22, 2005

(65) Prior Publication Data

US 2006/0003945 A1    Jan. 5, 2006

Related U.S. Application Data

(60) Provisional application No. 60/582,290, filed on Jun. 23, 2004.

(51) Int. Cl.
| | |
|---|---|
| *C07D 513/04* | (2006.01) |
| *C07D 209/08* | (2006.01) |
| *C07D 471/04* | (2006.01) |
| *A61K 31/4162* | (2006.01) |
| *A61P 25/18* | (2006.01) |

(52) U.S. Cl. ............ 514/233.2; 514/368; 514/300; 514/360; 514/254.02; 548/154; 548/151; 546/121; 544/318; 544/133

(58) Field of Classification Search .......... None
See application file for complete search history.

(56) References Cited

U.S. PATENT DOCUMENTS

| | | | |
|---|---|---|---|
| 3,489,767 | A | 1/1970 | Yamamoto et al. |
| 6,187,805 | B1 | 2/2001 | Pineiro et al. |
| 6,380,166 | B1 | 4/2002 | Miller et al. |
| 6,770,642 | B2* | 8/2004 | Cole et al. ............ 514/233.2 |
| 7,022,701 | B2* | 4/2006 | Cole et al. ............ 514/233.2 |

FOREIGN PATENT DOCUMENTS

| | | |
|---|---|---|
| JP | 43 024418 B | 1/1966 |
| WO | WO 2004/078719 A1 | 9/2004 |
| WO | WO 2005/009958 A1 | 2/2005 |
| WO | WO 2005/040112 A1 | 5/2005 |

OTHER PUBLICATIONS

Leenders, R. G. G., et al, *Synthesis*, 1996, 1309-1312.
Gum, A., et al *Chemistry: European Journal*, 2000, 6, 3714-3721.
Leenders, R. G. G., et al, *Bioorganic & Medicinal Chemistry*, 1999, 7, 1597-1610.
Slassi, A., et al., *Expert Opinion Therapeutic Patents*, 2002, 12(4): 513-527.
Leclerc, V., et al., *Journal of Medicinal Chemistry*, 2002, 45(9): 1853-59.
Sakamoto, T., et al., *Chemical and Pharmaceutical Bulletin*, 1994, 42(10): 2032-2035.

* cited by examiner

*Primary Examiner*—Patrick T Lewis
(74) *Attorney, Agent, or Firm*—Gloria K. Szakiel; David Kurlandsky; Scott Larsen

(57) ABSTRACT

The present invention provides a compound of formula I and the use thereof for the therapeutic treatment of disorders relating to or affected by the 5-HT6 receptor.

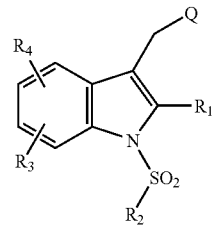

(I)

20 Claims, No Drawings

INDOLYLALKYLAMINE METABOLITES AS 5-HYDROXYTRYPTAMINE-6 LIGANDS

BACKGROUND OF THE INVENTION

This application claims the benefit under 35 U.S.C. §119(e) to co-pending U.S. provisional application No. 60/582,290, filed Jun. 23, 2004, which is hereby incorporated by reference in its entirety.

Various central nervous system disorders such as anxiety, depression, motor disorders, etc., are believed to involve a disturbance of the neurotransmitter 5-hydroxytryptamine (5-HT) or serotonin. Serotonin is localized in the central and peripheral nervous systems and is known to affect many types of conditions including psychiatric disorders, motor activity, feeding behavior, sexual activity, and neuroendocrine regulation among others. The effects of serotonin are regulated by the various 5-HT receptor subtypes. Known 5-HT receptors include the 5-HT1 family (e.g. 5-HT1A), the 5-HT2 family (e.g. 5-HT2A), 5-HT3, 5-HT4, 5-HT5, 5-HT6 and 5-HT7 subtypes.

The human 5-hydroxytryptamine-6 (5-HT6) receptor subtype has been cloned, and the extensive distribution of its mRNA has been reported. Highest levels of 5-HT6 receptor mRNA have been observed in the olfactory tubercle, the striatum, nucleus accumbens, dentate gyrus and CA1, CA2 and CA3 regions of the hippocampus. Lower levels of 5-HT6 receptor mRNA are seen in the granular layer of the cerebellum, several diencephalic nuclei, amygdala and in the cortex. Northern blots have revealed that 5-HT6 receptor mRNA appears to be exclusively present in the brain, with little evidence for its presence in peripheral tissues. The high affinity of a number of antipsychotic agents for the 5-HT6 receptor, in addition to its mRNA localization in striatum, olfactory tubercle and nucleus accumbens suggests that some of the clinical actions of these compounds may be mediated through this receptor. Therefore, 5-HT6 receptor ligands are believed to be of potential use in the treatment of certain CNS disorders such as anxiety, depression, epilepsy, obsessive compulsive disorder, attention deficit disorder, migraine, cognitive memory enhancement (e.g. for the treatment of Alzheimer's disease), sleep disorders, feeding disorders (e.g. anorexia or bulimia), neurodegenerative disorders (e.g. stroke or head trauma), panic attacks, withdrawal from drug abuse (e.g. cocaine, ethanol, nicotine or benzodiazepines), schizophrenia, or the like; or in the treatment of certain gastrointestinal disorders such as irritable bowel syndrome.

Indolylalkylamine derivatives such as those described in patent application publication U.S. 2003-0171353A-1 are potent and selective 5-HT6 ligands. Until now, metabolites of said indolylalkylamine derivatives have not been identified, isolated, purified or synthesized.

Therefore, it is an object of this invention to provide compounds which are metabolites of indolylalkylamine 5-HT6 ligands and which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders that are alleviated by 5-HT6 ligands.

It is a further object of this invention to provide a method to determine the metabolism of an indolylalkylamine derivative.

These and other objects and features of the invention will become more apparent by the detailed description set forth hereinbelow.

SUMMARY OF THE INVENTION

The present invention provides compound of formula I

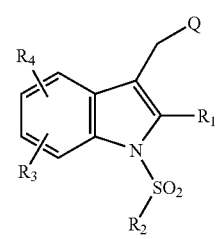

(I)

wherein
Q is $CO_2R_5$ or $CH_2NR_6COR_7$;
$R_1$ is H or $C_1$-$C_6$alkyl;
$R_2$ is an aryl or heteroaryl group each optionally substituted or an optionally substituted 8- to 13-membered bicyclic or tricyclic ring system having a N atom at the bridgehead and optionally containing 1, 2 or 3 additional heteroatoms selected from N, O or S;
$R_3$ and $R_4$ are each independently H, halogen, CN, $OCO_2R_8$, $CO_2R_9$, $CONR_{10}R_{11}$, $CNR_{12}NR_{13}R_{14}$, $SO_mR_{15}$, $NR_{16}R_{17}$, $OR_{18}$, $COR_{19}$ or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;
$R_5$ and $R_6$ are each independently H or $C_1$-$C_6$alkyl;
$R_7$ is $C_1$-$C_6$alkyl or

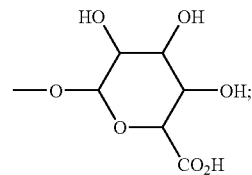

m is 0 or an integer of 1 or 2;
$R_8$, $R_9$, $R_{15}$ and $R_{19}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;
$R_{10}$, $R_{11}$ and $R_{18}$ are each independently H or a $C_1$-$C_6$alkyl, aryl or heteroaryl group each optionally substituted or $R_{10}$ and $R_{11}$ may be taken together with the atom to which they are attached to form a 5- to 7-membered ring optionally containing another heteroatom selected from O, N or S; and
$R_{12}$, $R_{13}$, $R_{14}$, $R_{16}$ and $R_{17}$ are each independently H or a $C_1$-$C_4$alkyl, aryl or heteroaryl group each optionally substituted; or $R_{13}$ and $R_{14}$ or $R_{16}$ and $R_{17}$ may be taken together with the atom to which they are attached to form a 5- to 7-membered ring optionally containing another heteroatom selected from O, N or S; or a stereoisomer thereof or a pharmaceutically acceptable salt thereof.

The present invention also provides methods and compositions useful for the therapeutic treatment of central nervous system disorders related to or affected by the 5-HT6 receptor and a method to determine the metabolism of an indolylalkylamine derivative.

DETAILED DESCRIPTION OF THE INVENTION

The ability of the 5-hydroxytryptamine-6 (5-HT6) receptor to bind a wide range of therapeutic compounds used in psychiatry, coupled with its intriguing distribution in the brain has stimulated significant interest in new compounds which are capable of interacting with or affecting said receptor. Significant efforts are being made to understand the possible role of the 5-HT6 receptor in psychiatry, cognitive dysfunction, motor function and control, memory, mood and the like. To that end, compounds which demonstrate a binding affinity for the 5-HT6 receptor are earnestly sought as potential therapeutic agents in the treatment of central nervous system disorders, for example see C. Reavill and D. C. Rogers, Current Opinion in Investigational Drugs, 2001, 2(1):104-109, Pharma Press Ltd.

Indolylalkylamine derivatives having a potent and selective binding affinity for the 5-HT6 receptor and their preparation are described in patent application publication U.S. 2003-0171353A-1, incorporated herein by reference thereto. Until now, metabolites of said indolylalkylamine derivatives have not been identified, isolated, purified or synthesized.

Surprisingly, it has now been found that compounds of formula I are metabolites of indolylalkylamine 5-HT6 derivatives. Advantageously, said formula I compounds may be used as effective therapeutic agents for the treatment of central nervous system (CNS) disorders associated with or affected by the 5-HT6 receptor. Accordingly, the present invention provides a compound of formula I

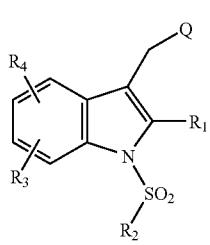

(I)

wherein

Q is $CO_2R_5$ or $CH_2NR_6COR_7$;

$R_1$ is H or $C_1$-$C_6$alkyl;

$R_2$ is an aryl or heteroaryl group each optionally substituted or an optionally substituted 8- to 13-membered bicyclic or tricyclic ring system having a N atom at the bridgehead and optionally containing 1, 2 or 3 additional heteroatoms selected from N, O or S;

$R_3$ and $R_4$ are each independently H, halogen, CN, $OCO_2R_8$, $CO_2R_9$, $CONR_{10}R_{11}$, $CNR_{12}NR_{13}R_{14}$, $SO_mR_{15}$, $NR_{16}R_{17}$, $OR_{18}$, $COR_{19}$ or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;

$R_5$ and $R_6$ are each independently H or $C_1$-$C_6$alkyl;

$R_7$ is $C_1$-$C_6$alkyl or

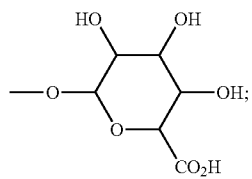

m is 0 or an integer of 1 or 2;

$R_8$, $R_9$, $R_{15}$ and $R_{19}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;

$R_{10}$, $R_{11}$ and $R_{18}$ are each independently H or a $C_1$-$C_6$alkyl, aryl or heteroaryl group each optionally substituted or $R_{10}$ and $R_{11}$ may be taken together with the atom to which they are attached to form a 5- to 7-membered ring optionally containing another heteroatom selected from O, N or S; and $R_{12}$, $R_{13}$, $R_{14}$, $R_{16}$ and $R_{17}$ are each independently H or a $C_1$-$C_4$alkyl, aryl or heteroaryl group each optionally substituted; or $R_{13}$ and $R_{14}$ or $R_{16}$ and $R_{17}$ may be taken together with the atom to which they are attached to form a 5- to 7-membered ring optionally containing another heteroatom selected from O, N or S; or a stereoisomer thereof or a pharmaceutically acceptable salt thereof.

As used in the specification and claims, the term halogen designates Br, Cl, I or F. The term cycloheteroalkyl designates a five- to seven-membered cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein X is NR, O or S; and R is H or an optional substituent as described hereinbelow:

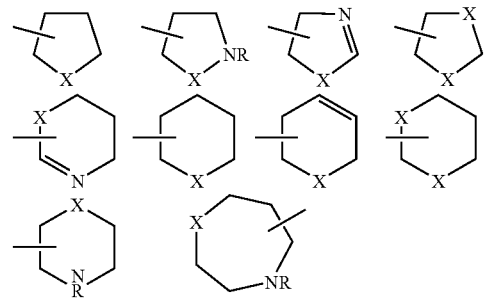

Similarly, as used in the specification and claims, the term heteroaryl designates a five- to ten-membered aromatic ring system containing 1, 2 or 3 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolyl, benzothienyl, benzofuranyl, benzisoxazolyl or the like. The term aryl designates a carbocyclic aromatic ring system such as phenyl, naphthyl, anthracenyl or the like. The term haloalkyl as used herein designates a $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different.

Exemplary of the 8- to 13-membered bicyclic or tricyclic ring systems having a N atom at a bridgehead and optionally containing 1, 2 or 3 additional heteroatoms selected from N, O or S included in the term as designated herein are the following ring systems wherein W is NR, O or S; and R is H or an optional substituent as described hereinbelow:

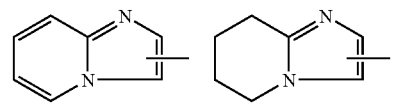

-continued

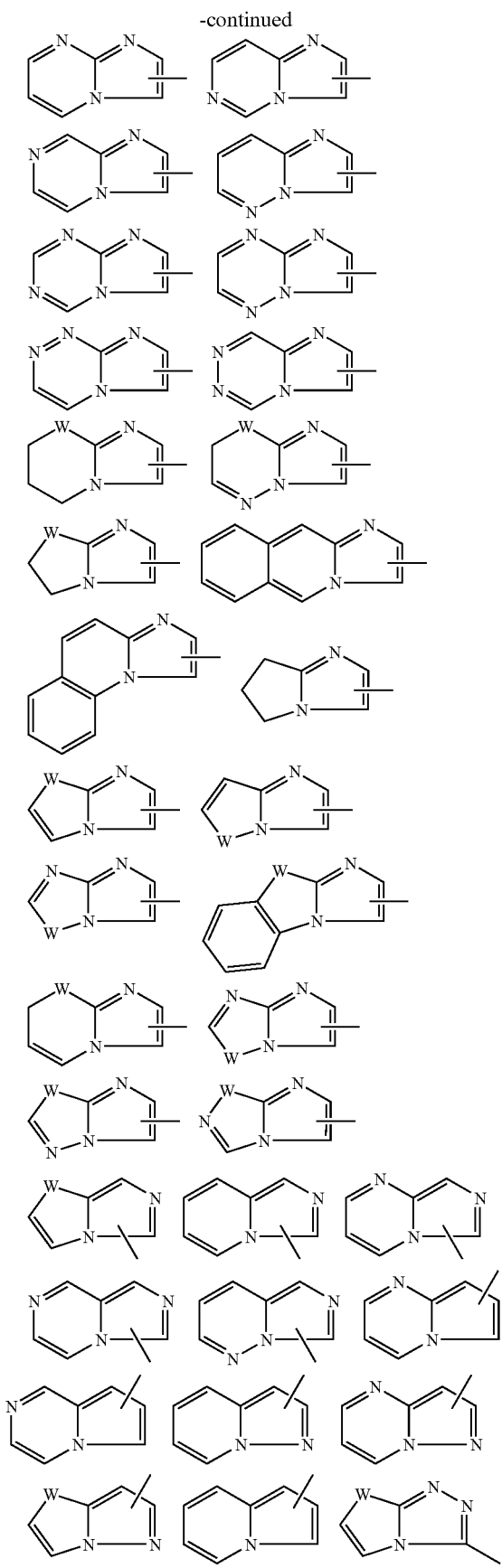

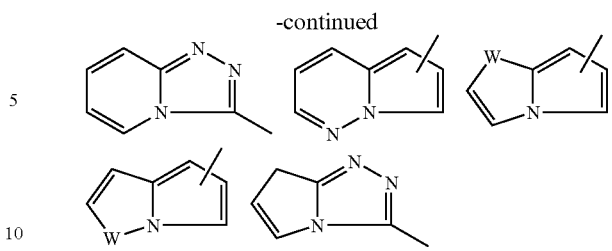

In the specification and claims, when the terms $C_1$-$C_6$alkyl, $C_2$-$C_6$alkenyl, $C_2$-$C_6$alkynyl, $C_3$-$C_7$cycloalkyl, cycloheteroalkyl, aryl, heteroaryl or 8- to 13-membered bicyclic or tricyclic ring system having a N atom at the bridgehead are designated as being optionally substituted, the substituent groups which are optionally present may be one or more, e.g. two or three, the same or different of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heteroaryl, cycloheteroalkyl or cycloalkyl groups, preferably halogen atoms or lower alkyl groups. Typically, 0-3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Compounds of the invention include amides, esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

When a compound of formula I contains one or more chiral centers or asymmetric carbons, then said formula I compound may exist as one or more stereoisomers. The various stereoisomers include enantiomers, diastereomers, atropisomers and geometric isomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of Formula I, the stereoisomers thereof and the pharmaceutically acceptable salts thereof. The compounds of the invention may be present as a mixture of stereoisomers, individual stereoisomers, or as an optically active form.

Preferred compounds of the invention are those compounds of formula I wherein $R_1$, $R_3$ and $R_4$ are H. Also preferred are those compounds of formula I wherein $R_2$ is an imidazolyl or imdazothiazolyl group each optionally substituted. Another group of preferred compounds of formula I are those compounds wherein Q is $CH_2NHCOCH_3$ or

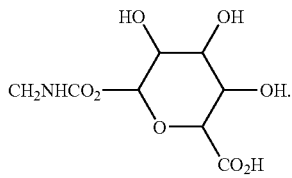

More preferred compounds of the invention are those compounds of formula I wherein $R_1$, $R_3$ and $R_4$ are H and $R_2$ is an imidazolyl or imdazothiazolyl group each optionally substituted. Another group of more preferred compounds are those compounds of formula I wherein $R_1$, $R_3$ and $R_4$ are H; $R_2$ is an imidazolyl or imdazothiazolyl group each optionally substituted; and Q is $CH_2NHCOCH_3$ or

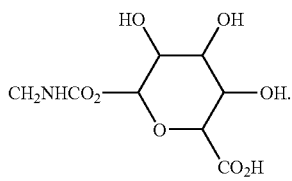

Among the preferred compounds of the invention are:
N-(2-{1-[(6-chloroimidazo[2,1-b][1,3]thiazol-5-yl)sulfonyl]-1H-indol-3-yl}ethyl)acetamide;
1-O-{[(2-{1-[(6-chloroimidazo[2,1-b][1,3]thiazol-5-yl)sulfonyl]-1H-indol-3-yl}ethyl)amino]carbonyl}-beta-D-glucopyranuronic acid;
{1-[(6-chloroimidazo[2,1-b][1,3]thiazol-5-yl)sulfonyl]-1H-indol-3-yl}acetic acid;
N-[(1-{[4-chloro-2-(methylthio)-1H-imidazol-5-yl]sulfonyl}-1H-indol-3-yl)methyl]acetamide; a stereoisomer thereof; or a pharmaceutically acceptable salt thereof.

Compounds of the invention may be conveniently prepared using conventional synthetic methods and, if required, standard separation and isolation techniques. For example, compounds of formula I wherein Q is $CO_2R_5$ (Ia) may be prepared by sequentially reacting an indole derivative of formula II with a strong base, such as n-butyllithium, KOt-Bu or NaH, and an arylsulfonyl halide, $ClSO_2R_2$ The reaction is shown in flow diagram I.

Flow Diagram I

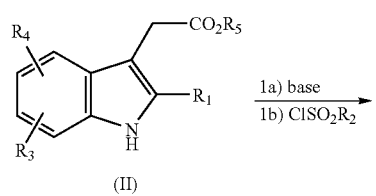

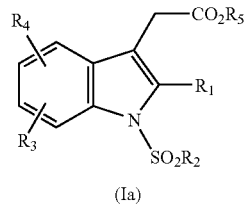

Compounds of formula I wherein Q is $CH_2NR_6COR_7$ and $R_7$ is $C_1$-$C_6$alkyl (Ib) may be prepared by reacting a compound of formula III with an anhydride of formula IV in the presence of a base, such as $N(C_2H_5)_3$ and optionally in the presence of a catalytic amount of 4-dimethylaminopyridine (DMAP). The reaction is shown in flow diagram II.

Flow Diagram II

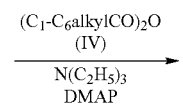

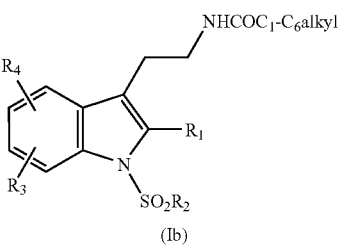

Compounds of formula I wherein Q is O-glucopyranuronic acid (Ic) may be prepared by reacting the compound of formula III with di-t-butyldicarbonate [$(Boc)_2O$] and $CH_3CN$ in the presence of a catalytic amount of DMAP to form the isocyanate of formula IV in situ and reacting said isocyanate with an hydroxyglucuronic ester of formula V to give the carbamoyl ester of formula VI and hydrolyzing said ester with a base, such as LiOH, to give the desired compound of formula Ic. The reaction sequence is shown in flow diagram III wherein Ac represents $COCH_3$.

Flow Diagram III

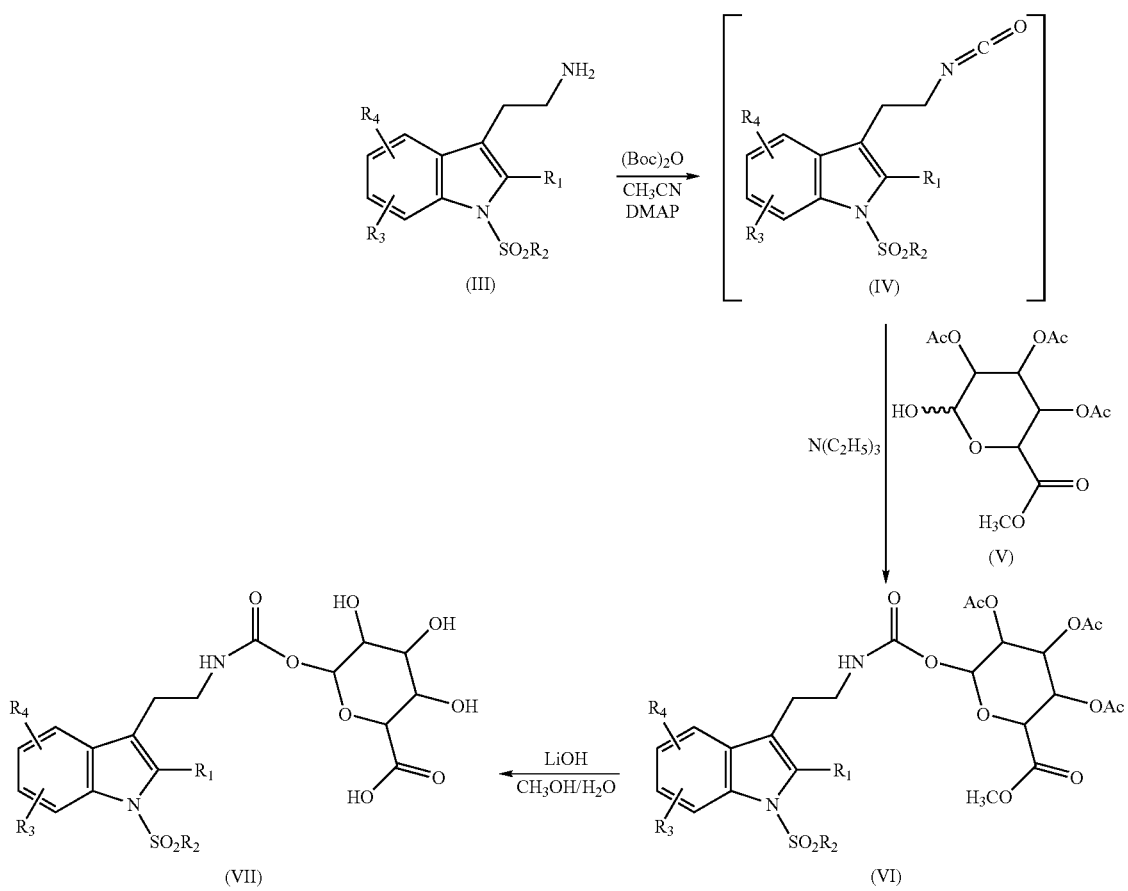

Compounds of formula II may be obtained from commercial sources or may be readily prepared using known synthetic methods, for example Baldi, B. G., et al, Journal of Labelled Compounds and Radiopharmaceuticals (1985), 22(3), 279-285 or Samizu, K. and Ogasawara, K., Synlett (1994), (7), 499-500.

Compounds of formula III and their preparation are described in U.S. 2003-0171353A-1, U.S. Pat. No. 6,187,805 and U.S. Pat. No. 6,403,808.

Alternatively, compounds of formula I may be obtained by providing an indolylalkylamine derivative, such as the compound of formula III, to a mammalian test subject and isolating the formula I compound from the plasma of said subject.

Advantageously, the formula I compounds of the invention are useful in the treatment of central nervous system disorders relating to or affected by the 5-HT6 receptor such as anxiety disorders, mood, psychiatric, cognitive or neurodegenerative disorders, or the like, for example, Alzheimer's disease, attention deficit disorder, acute anxiety disorder, general anxiety disorder, epilepsy, depression, obsessive compulsive disorder, migraine, sleep disorders, neurodegenerative disorders (such as head trauma or stroke), feeding disorders (such as anorexia or bulimia), schizophrenia, memory loss, disorders associated with withdrawl from drug or nicotine abuse, or the like or certain gastrointestinal disorders such as irritable bowel syndrome. Accordingly, the present invention provides a method for the treatment of a disorder of the central nervous system (CNS) related to or affected by the 5-HT6 receptor in a patient in need thereof which comprises providing said patient a therapeutically effective amount of a compound of formula I as described hereinabove. The compounds may be provided by oral or parenteral administration or in any common manner known to be an effective administration of a therapeutic agent to a patient in need thereof.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds, of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

Advantageously, compounds of formula I may be used for the identificaton or determination of the absorbtion or metabolism of an indolylalkylamine derivative. Accordingly, the present invention provides a method for the determination of the metabolism of a (1-arylsulfonyl-1H-indol-3-yl)ethylamine derivative which comprises evaluating a test sample for the presence of a compound of formula I.

For a more clear understanding, and in order to illustrate the invention more clearly, specific examples thereof are set forth hereinbelow. The following examples are merely illustrative and are not to be understood as limiting the scope and underlying principles of the invention in any way.

Unless otherwise stated, all parts are parts by weight. The terms NMR and HPLC designate nuclear magnetic resonance and high performance liquid chromatography, respectively. The term THF designates tetrahydrofuran.

EXAMPLE 1

Preparation of N-(2-{1-[(6-Chloro-imidazo[2,1-b][1,3]thiazol-5-yl)sulfonyl]-1H-indol-3-yl}-ethyl)acetamide

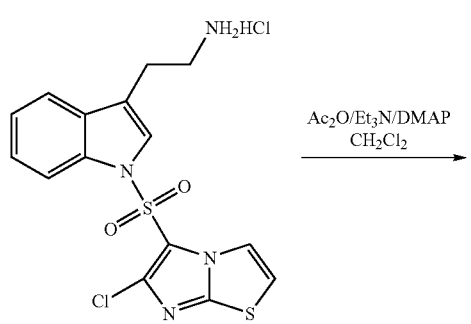

-continued

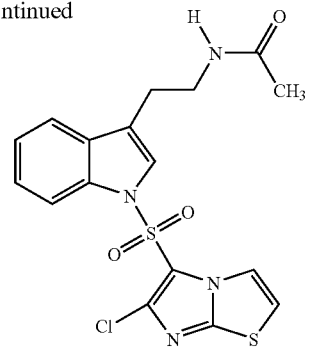

A stirred mixture of 2-{1-[(6-chloroimidazo[2,1-b][1,3]thiazol-5-yl)sulfonyl]-1H-indol-3-yl}ethylamine hydrochloride, 417 mg, 1.00 mmol) in dichloromethane and triethylamine (0.40 mL, 3.0 mmol) is treated with catalytic 4-dimethylaminopyridine (DMAP) (~5 mg) at room temperature under nitrogen. The heterogeneous mixture is treated with acetic anhydride (0.30 mL, 3.2 mmol) and the reaction becomes homogeneous. After 16 h, the reaction is treated with saturated aqueous $NaHCO_3$ (8 mL) for 0.3 h and then extracted with dichloromethane. The extracts are combined, dried over $MgSO_4$ and concentrated in vacuo to a foam. The foam is treated with 20:80 ethyl acetate:hexane and concentrated in vacuo to a solid. This is triturated with ether and filtered. The filtercake is dried to afford the title product as a white solid, 389 mg (92% yield), mp 150-152° C., characterized by CHN elemental analysis and $^1$H NMR.

EXAMPLE 2

Preparation of {1-[(6-Chloroimidazo[2,1-b][1,3]thiazol-5-yl)sulfonyl]-1H-indol-3-yl}acetic acid

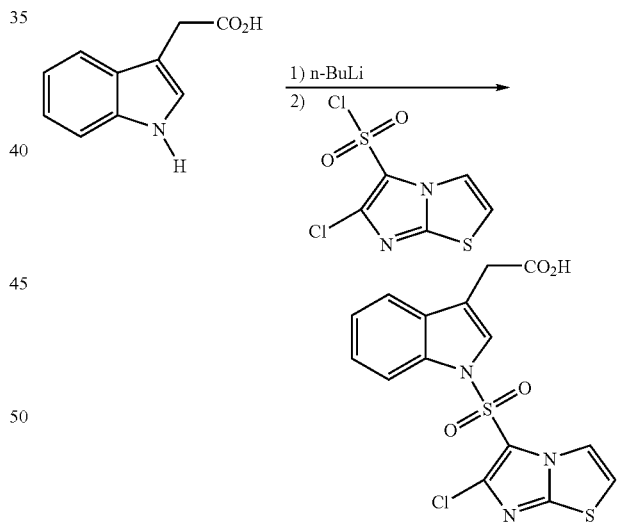

A stirred solution of 3-indolylacetic acid (175 mg, 1.00 mmol) in THF is cooled to −78° C. under nitrogen and treated portionwise with 2.5 M n-butyllithium in hexanes (0.84 mL, 2.10 mmol) over a 10 min. period. After 1 h at −78° C., the reaction mixture is treated with (6-chloroimidazo[2,1-b][1,3]thiazol-5-yl)sulfonyl chloride (257 mg, 1.00 mmol) in THF, allowed to warm to ambient temperature, stirred for 24 h and concentrated in vacuo. The resultant residue is treated with 1 M aq HCl (~2 mL) and water (3 mL) and extracted with dichloromethane. The extracts are combined, dried ($MgSO_4$) and concentrated in vacuo. Chromatography of this residue, eluting with ethyl acetate, affords the title compound as a light tan solid, 32 mg, mp 220-222° C. (darkens>200° C.), identified by mass spectral and NMR analyses.

EXAMPLE 3

Preparation of 3,4,5-Triacetoxy-6-(2-{1-[(6-chloroimidazo[2,1-b][1,3]thiazol-5-yl)sulfonyl]-1H-indol-3-yl}ethycarbamoyloxy)tetrahydropyran-2-carboxylic acid methyl ester

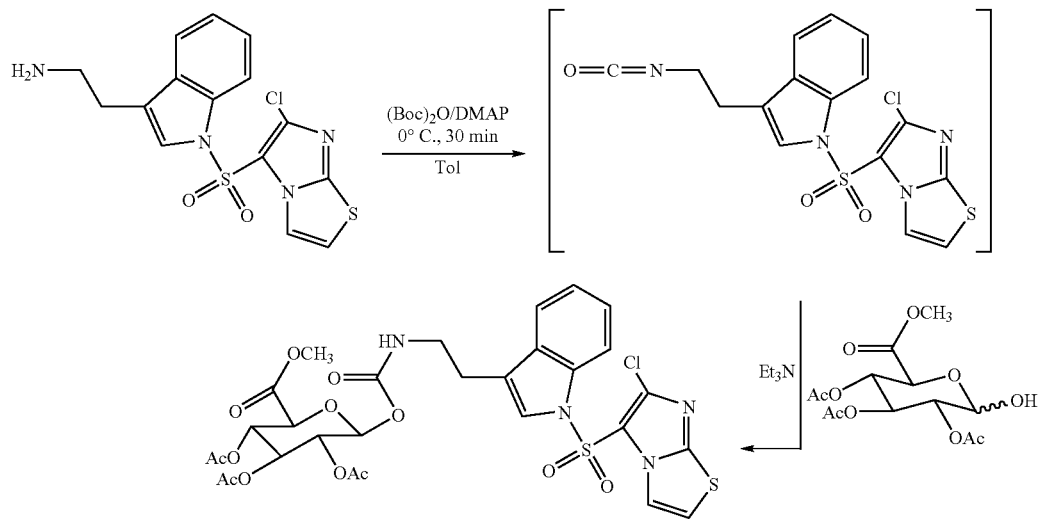

A solution of (Boc)₂O (1.8 g, 8.3 mmol, 1.2 eq) in CH₃CN is cooled to 0° C. (ice-water bath), treated dropwise with DMAP (203 mg, 1.66 mmol, 0.2 eq) in CH₃CN, stirred for 5 min, treated dropwise with 2-{1-[(6-chloroimidazo[2,1-b][1,3]thiazol-5-yl)sulfonyl]-1H-indol-3-yl}ethylamine (2.6 g, 6.9 mmol) in CH₃CN, stirred for 30 min (isocyanate is generated in situ) at 0° C., concentrated using rotavapor to remove the CH₃CN and chased with toluene. The resultant residue is dissolved in toluene, treated dropwise with a solution of hydroxyglucuronic ester (2.6 g, 7.7 mmol, 1.1 eq) in toluene followed by triethylamine (1.2 mL), stirred for 2 h at 0° C., allowed to warm to room temperature, stirred for 16 h and concentrated to dryness. This residue is purified by column chromatography (20-50% THF in heptane as eluent) to afford the pure β-anomer of the title product, 2 g (39% yield) and a mixture of α- and β-anomers (1:1.6), 2.5 g (49% yield). The anomers are identified by NMR analysis. $^1$H NMR (300 MHz, CDCl₃): β-anomer 4: 8.01 (d, 1H, J=4.5 Hz), 7.95-7.91 (m, 1H), 7.53-7.50 (m, 1H), 7.45 (s, 1H), 7.35-7.26 (2H, m), 7.17 (d, 1H, J=4.5 Hz), 5.74 (d, 1H, J=8.1 Hz), 5.36-5.09 (m, 3H), 4.99 (1H, m), 4.19 (d, 1H, J=9.9 Hz), 3.75 (s, 3H), 3.57-3.41 (2H, m), 2.92 (2H, t, J=7.0 Hz), 2.04, 2.03, 2.02 (3s, 9H). MS [M+H]⁺=741. α-anomer (200 mg, contains 2% β-anomer) $^1$H NMR (300 MHz, CDCl₃): 8.03 (d, 1H, J=4.2 Hz), 7.94-7.91 (m, 1H), 7.56-7.53 (m, 1H), 7.45 (s, 1H), 7.35-7.26 (2H, m), 7.14 (d, 1H, J=4.8 Hz), 6.33 (d, 1H, J=3.6 Hz), 5.52-5.46 (m, 1H), 5.26-5.10 (3H, m), 4.38 (d, 1H, J=10.2 Hz), 3.74 (s, 3H), 3.57-3.46 (2H, m), 2.92 (2H, t, J=7.0 Hz), 2.03 (3s, 9H).

EXAMPLE 4

Preparation of 1-O-{[(2-{1-[(6-Chloroimidazo[2,1-b][1,3]thiazol-5-yl)sulfonyl]-1H-indol-3-yl}ethyl)amino]carbonyl}-beta-D-glucopyranuronic acid

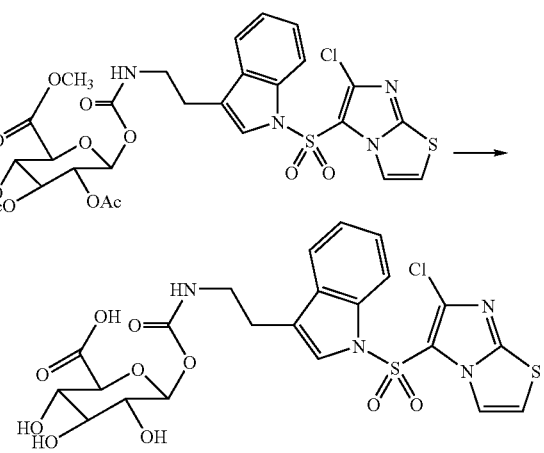

A solution of 3,4,5-triacetoxy-6-(2-{1-[(6-chloroimidazo[2,1-b][1,3]thiazol-5-yl)sulfonyl]-1H-indol-3-yl}ethycarbamoyloxy)tetrahydropyran-2-carboxylic acid methyl ester (1.0 g, 1.35 mmol) in THF is treated with CH₃OH (38.8 mL) and H₂O (10 mL), cooled to 0° C. (ice-water bath), treated with a solution of LiOH.H₂O (340 mg, 8.1 mmol, 6 eq) in H$_2$O (5.5 mL) [0.1 N LiOH/MeOH/THF/H$_2$O] and stirred at 0° C. for 2 h under N$_2$ atmosphere. Progress of the deprotection is monitored via reversed-phase TLC (SiO$_2$—C18 MeCN/H$_2$O, 3/7). The reaction mixture is diluted with 150 mL of H$_2$O, neutralized by the addition of 10 g of amberlite-120 (plus) cation exchange material (H$^+$ form) and filtered. The filtrate is concentrated under reduced pressure to an aqueous suspension. This suspension is freeze dried and lyophilized to give the title product, 700 mg (86% yield). Further purification by silica gel column chromatography [CHCl$_3$/CH$_3$OH/H$_2$O (7:3:0.5) as a eluent] provides the title product, 310 mg, 98% pure, identified by mass spectral and NMR analyses. $^1$H NMR (300 MHz, DMSO-d$_6$): 8.31 (d, 1H, J=4.5 Hz), 7.94-7.91 (m, 1H), 7.82 (s, 1H), 7.69 (d, 1H, J=4.2 Hz), 7.64-7.57 (m, 2H), 7.39-7.27 (m, 2H), 5.31 (d, 1H, J=8.1 Hz), 3.69 (d, 1H, J=9.0 Hz), 3.37-3.13 (m, 5H), 2.82 (t, 2H, J=7.0 Hz); $^{13}$C (75 MHz, DMSO-d$_6$): 170.6, 155.4, 155.3, 152.3, 139.2, 134.9, 131.6, 125.7, 124.5, 124.4, 121.1, 121.1, 120.7, 118.8, 116.6, 113.8, 95.5, 76.6, 76.5, 72.8, 72.0, 25.2; LC/MS (ESI) retention time=35.12, [M+H]$^+$=600.7.

The α-anomer (57 mg) is obtained in the same manner described above, identified by HPLC and mass spectral analyses. LC/MS (ESI) retention time=27.11 min, [M+H]$^+$=600.8.

EXAMPLE 5

Comparative Evaluation of 5-HT6 Binding Affinity of Test Compounds

The affinity of test compounds for the serotonin 5-HT6 receptor is evaluated in the following manner. Cultured Hela cells expressing human cloned 5-HT6 receptors are harvested and centrifuged at low speed (1,000× g) for 10.0 min to remove the culture media. The harvested cells are suspended in half volume of fresh physiological phosphate buffered saline solution and recentrifuged at the same speed. This operation is repeated. The collected cells are then homogenized in ten volumes of 50 mM Tris.HCl (pH 7.4) and 0.5 mM EDTA. The homogenate is centrifuged at 40,000× g for 30.0 min and the precipitate is collected. The obtained pellet is resuspended in 10 volumes of Tris.HCl buffer and recentrifuged at the same speed. The final pellet is suspended in a small volume of Tris.HCl buffer and the tissue protein content is determined in aliquots of 10-25 μl volumes. Bovine Serum Albumin is used as the standard in the protein determination according to the method described in Lowry et al., *J. Biol. Chem.*, 193:265 (1951). The volume of the suspended cell membranes is adjusted to give a tissue protein concentration of 1.0 mg/ml of suspension. The prepared membrane suspension (10 times concentrated) is aliquoted in 1.0 ml volumes and stored at −70° C. until used in subsequent binding experiments.

Binding experiments are performed in a 96 well microtiter plate format, in a total volume of 200 μl. To each well is added the following mixture: 80.0 μl of incubation buffer made in 50 mM Tris.HCl buffer (pH 7.4) containing 10.0 mM MgCl$_2$ and 0.5 mM EDTA and 20 μl of [$^3$H]-LSD (S.A., 86.0 Ci/mmol, available from Amersham Life Science), 3.0 nM. The dissociation constant, K$_D$ of the [$^3$H]LSD at the human serotonin 5-HT6 receptor is 2.9 nM, as determined by saturation binding with increasing concentrations of [$^3$H]LSD. The reaction is initiated by the final addition of 100.0 μl of tissue suspension. Nonspecific binding is measured in the presence of 10.0 μM methiothepin. The test compounds are added in 20.0 μl volume.

The reaction is allowed to proceed in the dark for 120 min at room temperature, at which time, the bound ligand-receptor complex is filtered off on a 96 well unifilter with a Packard Filtermate® 196 Harvester. The bound complex caught on the filter disk is allowed to air dry and the radioactivity is measured in a Packard TopCount® equipped with six photomultiplier detectors, after the addition of 40.0 μl Microscint®-20 scintillant to each shallow well. The unifilter plate is heat-sealed and counted in a PackardTopCount® with a tritium efficiency of 31.0%.

Specific binding to the 5-HT6 receptor is defined as the total radioactivity bound less the amount bound in the presence of 10.0 μM unlabeled methiothepin. Binding in the presence of varying concentrations of test compound is expressed as a percentage of specific binding in the absence of test compound. The results are plotted as log % bound versus log concentration of test compound. Nonlinear regression analysis of data points with a computer assisted program Prism® yielded both the IC$_{50}$ and the K$_I$ values of test compounds with 95% confidence limits. A linear regression line of data points is plotted, from which the IC$_{50}$ value is determined and the K$_I$ value is determined based upon the following equation:

$$K_I = IC_{50}/(1+L/K_D)$$

where L is the concentration of the radioactive ligand used and K$_D$ is the dissociation constant of the ligand for the receptor, both expressed in nM.

Using this assay, the following Ki values are determined and compared to those values obtained by representative compounds known to demonstrate binding to the 5-HT6 receptor. The data are shown in Table I, below.

TABLE I

| Test Compound (Ex. No.) | 5-HT6 Binding Ki (nM) |
| --- | --- |
| 1 | 26 |
| 2 | 248 |
| 4 | |
| Comparative Examples | |
| Clozapine | 6.0 |
| Loxapine | 41.4 |
| Bromocriptine | 23.0 |
| Methiothepin | 8.3 |
| Mianserin | 44.2 |
| Olanzepine | 19.5 |

As can be seen from the results set forth above, the compounds of the present invention demonstrate significant affinity for the 5-HT6 receptor.

What is claimed is:
1. A compound of formula I

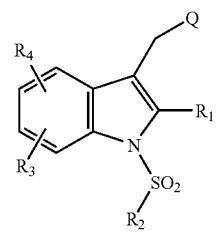

(I)

wherein
  Q is CO$_2$R$_5$ or CH$_2$NR$_6$COR$_7$;
  R$_1$ is H or C$_1$-C$_6$alkyl;
  R$_2$ is an aryl or heteroaryl group each optionally substituted or an optionally substituted 8- to 13-membered bicyclic or tricyclic ring system having a N atom at the bridgehead and optionally containing 1, 2 or 3 additional heteroatoms selected from N, O or S;

$R_3$ and $R_4$ are each independently H, halogen, CN, $OCO_2R_8$, $CO_2R_9$, $CONR_{10}R_{11}$, $CNR_{12}NR_{13}R_{14}$, $SO_mR_{15}$, $NR_{16}R_{17}$, $OR_{18}$, $COR_{19}$ or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;

$R_5$ and $R_6$ are each independently H or $C_1$-$C_6$alkyl;

$R_7$ is $C_1$-$C_6$alkyl or

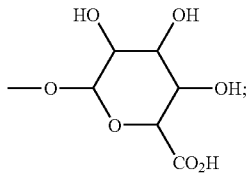

m is 0 or an integer of 1 or 2;

$R_8$, $R_9$, $R_{15}$ and $R_{19}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;

$R_{10}$, $R_{11}$ and $R_{18}$ are each independently H or a $C_1$-$C_6$alkyl, aryl or heteroaryl group each optionally substituted or $R_{10}$ and $R_{11}$ may be taken together with the atom to which they are attached to form a 5- to 7-membered ring optionally containing another heteroatom selected from O, N or S; and $R_{12}$, $R_{13}$, $R_{14}$, $R_{16}$ and $R_{17}$ are each independently H or a $C_1$-$C_4$alkyl, aryl or heteroaryl group each optionally substituted; or $R_{13}$ and $R_{14}$ or $R_{16}$ and $R_{17}$ may be taken together with the atom to which they are attached to form a 5- to 7-membered ring optionally containing another heteroatom selected from O, N or S; or a stereoisomer thereof or a pharmaceutically acceptable salt thereof.

2. The compound according to claim 1 wherein $R_1$, $R_3$ and $R_4$ are H.

3. The compound according to claim 2 wherein $R_2$ is an imidazolyl or imidazothiozolyl group each optionally substituted.

4. The compound according to claim 3 wherein Q is $CO_2H$, $CH_2NHCOCH_3$ or

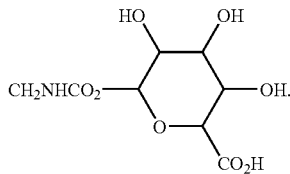

5. The compound according to claim 4 selected from the group consisting of:

N-(2-{1-[(6-chloroimidazo[2,1-b][1,3]thiazol-5-yl)sulfonyl]-1H-indol-3-yl}ethyl)acetamide;

1-O-{[(2-{1-[(6-chloroimidazo[2,1-b][1,3]thiazol-5-yl)sulfonyl]-1H-indol-3-yl}ethyl)amino]carbonyl}-beta-D-glucopyranuronic acid;

{1-[(6-chloroimidazo[2,1-b][1,3]thiazol-5-yl)sulfonyl]-1H-indol-3-yl}acetic acid;

N-[(1-{[4-chloro-2-(methylthio)-1H-imidazol-5-yl]sulfonyl}-1H-indol-3-yl)methyl]acetamide;

a stereoisomer thereof; and
a pharmaceutically acceptable salt thereof.

6. The compound according to claim 5 N-(2-{1-[(6-chloroimidazo[2,1-b][1,3]thiazol-5-yl)sulfonyl]-1H-indol-3-yl}ethyl)acetamide.

7. The compound according to claim 5 1-O-{[(2-{1-[(6-chloroimidazo[2,1-b][1,3]thiazol-5-yl)sulfonyl]-1H-indol-3-yl}ethyl)amino]carbonyl}-beta-D-glucopyranuronic acid.

8. A method for the treatment of a disorder of the central nervous system related to or affected by the 5-HT6 receptor in a patient in need thereof which comprises providing to said patient a therapeutically effective amount of a compound of formula I

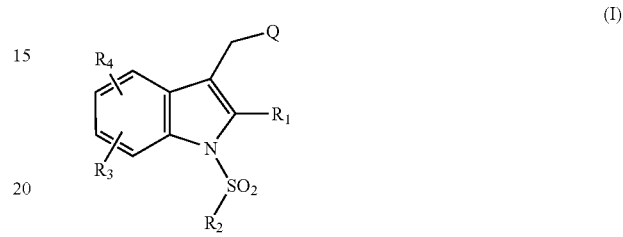

wherein

Q is $CO_2R_5$ or $CH_2NR_6COR_7$;

$R_1$ is H or $C_1$-$C_6$alkyl;

$R_2$ is an aryl or heteroaryl group each optionally substituted or an optionally substituted 8- to 13-membered bicyclic or tricyclic ring system having a N atom at the bridgehead and optionally containing 1, 2 or 3 additional heteroatoms selected from N, O or S;

$R_3$ and $R_4$ are each independently H, halogen, CN, $OCO_2R_8$, $CO_2R_9$, $CONR_{10}R_{11}$, $CNR_{12}NR_{13}R_{14}$, $SO_mR_{15}$, $NR_{16}R_{17}$, $OR_{18}$, $COR_{19}$ or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;

$R_5$ and $R_6$ are each independently H or $C_1$-$C_6$alkyl;

$R_7$ is $C_1$-$C_6$alkyl or

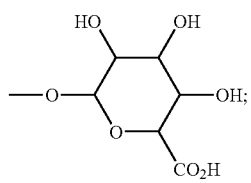

m is 0 or an integer of 1 or 2;

$R_8$, $R_9$, $R_{15}$ and $R_{19}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;

$R_{10}$, $R_{11}$ and $R_{18}$ are each independently H or a $C_1$-$C_6$alkyl, aryl or heteroaryl group each optionally substituted or $R_{10}$ and $R_{11}$ may be taken together with the atom to which they are attached to form a 5- to 7-membered ring optionally containing another heteroatom selected from O, N or S; and $R_{12}$, $R_{13}$, $R_{14}$, $R_{16}$ and $R_{17}$ are each independently H or a $C_1$-$C_4$alkyl, aryl or heteroaryl group each optionally substituted; or $R_{13}$ and $R_{14}$ or $R_{16}$ and $R_{17}$ may be taken together with the atom to which they are attached to form a 5- to 7-membered ring optionally containing another heteroatom selected from O, N or S; or a stereoisomer thereof or a pharmaceutically acceptable salt thereof.

9. The method according to claim 8 wherein said disorder is a neurodegenerative disorder.

10. The method according to claim 8 wherein said disorder is an anxiety disorder or a cognitive disorder.

11. The method according to claim 10 wherein said disorder is attention deficit disorder, obsessive compulsive disorder or general anxiety disorder.

12. The method according to claim 8 having a formula I compound wherein $R_1$, $R_3$ and $R_4$ are H; $R_2$ is an imidazolyl or imidazothioazolyl group each optionally substituted; and Q is $CH_2NHCOCH_3$ or $$CH_2NHCO_2-\begin{array}{c}HO\quad OH\\ \diagdown\diagup\\ \text{(pyranose ring)}\\ \diagup\diagdown\\ CO_2H\end{array}-OH.$$

13. The method according to claim 12 having the formula I compound N-(2-{1-[(6-chloroimidazo[2,1-b][1,3]thiazol-5-yl)sulfonyl]-1H-indol-3-yl}ethyl)acetamide.

14. The method according to claim 12 having the formula I compound 5 1-O-{[(2-{1-[(6-chloroimidazo[2,1-b][1,3]thiazol-5-yl)sulfonyl]-1H-indol-3-yl}ethyl)amino]-carbonyl}-beta-D-glucopyranuronic acid.

15. A pharmaceutical composition which comprises a pharmaceutically acceptable carrier and an effective amount of a compound of formula I (I)

[indole structure with $R_4$, $R_3$, $R_1$, $SO_2$, $R_2$, and Q substituents]

wherein
Q is $CO_2R_5$ or $CH_2NR_6COR_7$;
$R_1$ is H or $C_1$-$C_6$alkyl;
$R_2$ is an aryl or heteroaryl group each optionally substituted or an optionally substituted 8- to 13-membered bicyclic or tricyclic ring system having a N atom at the bridgehead and optionally containing 1, 2 or 3 additional heteroatoms selected from N, O or S;
$R_3$ and $R_4$ are each independently H, halogen, CN, $OCO_2R_8$, $CO_2R_9$, $CONR_{10}R_{11}$, $CNR_{12}NR_{13}R_{14}$, $SO_mR_{15}$, $NR_{16}R_{17}$, $OR_{18}$, $COR_{19}$ or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;
$R_5$ and $R_6$ are each independently H or $C_1$-$C_6$alkyl;
$R_7$ is $C_1$-$C_6$alkyl or $$-O-\begin{array}{c}HO\quad OH\\ \diagdown\diagup\\ \text{(pyranose ring)}\\ \diagup\diagdown\\ CO_2H\end{array}-OH;$$

m is 0 or an integer of 1 or 2;
$R_8$, $R_9$, $R_{15}$ and $R_{19}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;
$R_{10}$, $R_{11}$ and $R_{18}$ are each independently H or a $C_1$-$C_6$alkyl, aryl or heteroaryl group each optionally substituted or $R_{10}$ and $R_{11}$ may be taken together with the atom to which they are attached to form a 5- to 7-membered ring optionally containing another heteroatom selected from O, N or S; and
$R_{12}$, $R_{13}$, $R_{14}$, $R_{16}$ and $R_{17}$ are each independently H or a $C_1$-$C_4$alkyl, aryl or heteroaryl group each optionally substituted; or $R_{13}$ and $R_{14}$ or $R_{16}$ and $R_{17}$ may be taken together with the atom to which they are attached to form a 5- to 7-membered ring optionally containing another heteroatom selected from O, N or S; or
a stereoisomer thereof or a pharmaceutically acceptable salt thereof.

16. The composition according to claim 15 having a formula I compound wherein $R_1$, $R_3$ and $R_4$ are H.

17. The composition according to claim 16 having a formula I compound wherein $R_2$ is an imidazolyl or imidazothiazolyl group each optionally substituted.

18. The composition according to claim 17 having a formula I compound wherein Q is $CO_2H$, $CH_2NHCOCH_3$ or $$CH_2NHCO_2-\begin{array}{c}HO\quad OH\\ \diagdown\diagup\\ \text{(pyranose ring)}\\ \diagup\diagdown\\ CO_2H\end{array}-OH.$$

19. The composition according to claim 18 having a formula I compound selected from the group consisting of:
N-(2-{1-[(6-chloroimidazo[2,1-b][1,3]thiazol-5-yl)sulfonyl]-1H-indol-3-yl}ethyl)acetamide;
1-O-{[(2-{1-[(6-chloroimidazo[2,1-b][1,3]thiazol-5-yl)sulfonyl]-1H-indol-3-yl}ethyl)amino]carbonyl}-beta-D-glucopyranuronic acid;
{1-[(6-chloroimidazo[2,1-b][1,3]thiazol-5-yl)sulfonyl]-1H-indol-3-yl}acetic acid;
N-[(1-{[4-chloro-2-(methylthio)-1H-imidazol-5-yl]sulfonyl}-1H-indol-3-yl)methyl]acetamide;
a stereoisomer thereof; and
a pharmaceutically acceptable salt thereof.

20. A method for the determination of the metabolism of a (1-arylsulfonyl-1H-indol-3-yl)ethylamine derivative which comprises evaluating a test sample for the presence of a compound of formula I (I)

[indole structure with $R_4$, $R_3$, $R_1$, $SO_2$, $R_2$, and Q substituents]

wherein
Q is $CO_2R_5$ or $CH_2NR_6COR_7$;
$R_1$ is H or $C_1$-$C_6$alkyl;
$R_2$ is an aryl or heteroaryl group each optionally substituted or an optionally substituted 8- to 13-membered bicyclic or tricyclic ring system having a N atom at the bridgehead and optionally containing 1, 2 or 3 additional heteroatoms selected from N, O or S;

$R_3$ and $R_4$ are each independently H, halogen, CN, $OCO_2R_8$, $CO_2R_9$, $CONR_{10}R_{11}$, $CNR_{12}NR_{13}R_{14}$, $SO_mR_{15}$, $NR_{16}R_{17}$, $OR_{18}$, $COR_{19}$ or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;

$R_5$ and $R_6$ are each independently H or $C_1$-$C_6$alkyl;

$R_7$ is $C_1$-$C_6$alkyl or

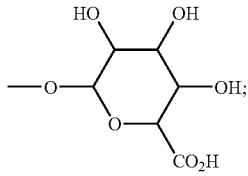

m is 0 or an integer of 1 or 2;

$R_8$, $R_9$, $R_{15}$ and $R_{19}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;

$R_{10}$, $R_{11}$ and $R_{18}$ are each independently H or a $C_1$-$C_6$alkyl, aryl or heteroaryl group each optionally substituted or $R_{10}$ and $R_{11}$ may be taken together with the atom to which they are attached to form a 5- to 7-membered ring optionally containing another heteroatom selected from O, N or S; and $R_{12}$, $R_{13}$, $R_{14}$, $R_{16}$ and $R_{17}$ are each independently H or a $C_1$-$C_4$alkyl, aryl or heteroaryl group each optionally substituted; or $R_{13}$ and $R_{14}$ or $R_{16}$ and $R_{17}$ may be taken together with the atom to which they are attached to form a 5- to 7-membered ring optionally containing another heteroatom selected from O, N or S; or a stereoisomer thereof;

wherein said evaluating comprises identifying the presence of a compound of formula I in the test sample by nuclear magnetic resonance analysis, high performance liquid chromatography analysis, mass spectral analysis or a combination thereof.

* * * * *